(12) United States Patent
Golemi-Kotra et al.

(10) Patent No.: US 7,393,918 B2
(45) Date of Patent: Jul. 1, 2008

(54) PROTEIN BINDING MINIATURE PROTEINS AND USES THEREOF

(75) Inventors: Dasantila Golemi-Kotra, Thornhill (CA); Alanna S. Schepartz Shrader, Wilton, CT (US)

(73) Assignee: Yale University, New Haven, CT (US)

( * ) Notice: Subject to any disclaimer, the term of this patent is extended or adjusted under 35 U.S.C. 154(b) by 59 days.

(21) Appl. No.: 11/009,101

(22) Filed: Dec. 10, 2004

(65) Prior Publication Data

US 2005/0287643 A1  Dec. 29, 2005

Related U.S. Application Data

(60) Provisional application No. 60/529,401, filed on Dec. 11, 2003.

(51) Int. Cl.
  C07K 14/00  (2006.01)
(52) U.S. Cl. .................................................. 530/300
(58) Field of Classification Search ................ 435/69.1; 514/2–21
  See application file for complete search history.

(56) References Cited

FOREIGN PATENT DOCUMENTS

WO   WO 0181375 A2   11/2001
WO   WO 03/053996    7/2003

OTHER PUBLICATIONS

Chin, J. W. et al., "Concerted evolution of structure and function in a Miniature Protein", Journal of the American Chemical Society, American Chemical Society, 123:2929-2930 (2001).
Golemi-Kotra D. et al., "High Affinity, Paralog-specific Recognition of the Mena EVH1 Domain by a Miniature Protein," Journal of the American Chemical Society, 126(1):4-5 (2004).
Rutledge, Stacey E. et al., "Molecular recognition of protein surfaces: high affinity ligands for the CBP KIX domain", Journal of the American Chemical Society, 125:14336-14347 (2003).
Armstrong, K.M., et al., "The (i, i+4) Phe-His Interaction Studies in an Alanine-based α-Helix," J. Mol. Biol., 230:284-291, (1993).
Aszódi, A., et al., "The vasodilator-stimulated phosphoprotein (VASP) is involved in cGMP-and cAMP-mediated inhibition of agonist-induced platelet aggregation, but is dispensable for smooth muscle function," Embo J., 18:37-48 (1999).
Bachmann, C., et al., "The EVH2 Domain of the Vasodilator-stimulated Phosphoprotein Mediates Tetramerization, F-actin Binding, and Actin Bundle Formation," J. Biol. Chem., 274:23549-23557 (1999).
Ball, L.J., et al., "EVH1 domains: structure, function and interactions," Febs Lett., 513:45-52 (2002).
Blundell, T.L., et al., "X-ray analysis (1.4-A resolution) of avian pancreatic polypeptide: Small globular protein hormone," Proc. Natl. Acad. Sci., 78(7):4175-4179, USA, (1981).
Callebaut, I., et al., "EVH1/WH1 domains of VASP and WASP proteins belong to a large family including Ran-binding domains of the RanBP1 family," Febs Lett. 441:181-185 (1998).
Cameron, L.A., et al., "Secrets of actin-based motility revealed by a bacterial pathogen," Nat. Rev. Mol. Cell. Biol., 1:110-119 (2000).
Carl, U.D., et al., "Aromatic and basic residues within the EVH1 domain of VASP specify its interaction with proline-rich ligands," Curr. Biol., 9:715-718 (1999).
Chin et al., "Methodology for Optimizing Functional Miniature Proteins Based on Avian Pancreatic Polypeptide Using Phage Display", Bioorg. Med. Chem. Lett., 11:1501-1505 (2001).
Chin, J.W., et al., "Design and Evolution of a Miniature Bcl-2 Binding Protein," Angew Chem. Int. Ed. Engl., 40(20):3806-3809 (2001).
Cunningham, B.C. and Wells, J.A., "Minimized proteins," Curr. Opin. Struct. Biol., 7:457-462 (1997).
Ermekova, K.S., et al., "The WW Domain of Neural Protein FE65 Interacts with Proline-rich Motifs in Mena, the Mammalian Homolog of *Drosophila* Enabled," J. Biol. Chem, 272(52):32869-32877 (1997).
Gertler, F.B., et al., "enabled, a dosage-sensitive suppressor of mutations in the *Drosophila* Abl tyrosine kinase, encodes an Abl substrate with SH3 domain-binding properties," (abstract) Genes Dev., 9:521-533 (1995).
Gertler, F.B., et al., "Genetic Suppression of Mutations in the *Drosop abl* Proto-Oncogene Homolog," Science, 248(4957):857-860 (1989).
Gertler, F.B., et al., "Mena, a Relative of VASP and *Drosophila* Enabled, Is Implicated in the Control of Microfilament Dynamics," Cell, 87:227-239 (1996).
Haffner, C., et al., "Molecular cloning, structural analysis and functional expression of the proline-rich focal adhesion and microfilament-associated protein VASP," Embo J., 14(1):19-27 (1995).
Halbrugge, M. and Walter, U., "Analysis, purification and properties of a 50 000-dalton membrane-associated phosphoprotein from human platelets," J. Chromatogr., 521:335-343 (1990).
Halbrugge, M., and Walter, U., "Purification of a vasodilator-regulated phosphoprotein from human platelets," Eur. J. Biochem, 185:41-50 (1989).
Huttelmaier, S., et al., "Characterization of the actin binding properties of the vasodilator-stimulated phosphoprotein VASP," FEBS Lett., 451:68-74 (1999).
Kocks, C., et al., "L. monocytogenes-Induced Actin Assembly Requires the *actA* Gene Product, a Surface Protein," Cell, 68:521-531 (1992).
Koehler et al., "Discovery of an Inhibitor of a Transcription Factor Using Small Molecule Microarrays and Diversity-Oriented Syntheses", J. Am. Chem. Soc., 125:8420-8421 (2003).

(Continued)

Primary Examiner—Maryam Monshipouri
Assistant Examiner—Marsha Tsay
(74) Attorney, Agent, or Firm—Wolf, Greenfield & Sacks, P.C.

(57) ABSTRACT

In certain aspects, the present invention provides miniature proteins resulted from a protein scaffold such as an avian pancreatic polypeptide that can be modified by substitution of at least one amino acid residue. In other aspects, the present invention provides diagnostic and therapeutic uses of these miniature proteins.

13 Claims, 2 Drawing Sheets

OTHER PUBLICATIONS

Lanier, L.M., et al., "Mena Is Required for Neurulation and Commissure Formation," Neuron, 22;313-325 (1999).

Laurent, v., et al., "Role of Proteins of the Ena/VASP Family in Actin-based Motility of *Listeria monocytogenes*," J. Cell. Biol., 144(6):1245-1258 (1999).

Loisel, T.P., et al., "Reconstitution of actin-based motility of *Listeria* and *Shigella* using pure proteins," Nature 401:613-616 (1999).

Montclare, J.K. and Schepartz, A., "Miniature Homeodomains: High Specificity without an N-Terminal Arm," J. Am. Chem. Soc., 125:3416-3417 (2003).

Niebuhr, K., et al., "A novel proline-rich motif present in ActA of *Listeria monocytogenes* and cytoskeletal proteins is the ligand for the EVH1 domain, a protein module present in the Ena/VASP family," Embo J., 16(17):5433-5444 (1997).

Pistor, S., et al., "The bacterial actin nucleator protein ActA of *Listeria monocytogenes* contains multiple binding sites for host microfilament proteins," Curr. Biol., 5:517-525 (1995).

Prehoda, K.E., et al., "Structure of the Enabled/VASP Homology 1 Domain-Peptide Complex: A Key Component in the Spatial Control of Actin Assembly," Cell, 97:471-480 (1999).

Reinhard, M., et al., "Identification, purification, and characterization of a zyxin-related protein that binds the focal adhesion and microfilament protein VASP (vasodilator-stimulated phosphoprotein)," Proc. Natl. Acad. Sci. USA, 92:7956-7960 (1995).

Reinhard, M., et al., "The 46/50 kDa phosphoprotein VASP purified from human platelets is a novel protein associated with actin filaments and focal contacts," Embo J., 11(6):2063-2070 (1992).

Smith, G.A., et al., "The Tandem Repeat Domain in the *Listeria monocytogenes* ActA Protein Controls the Rate of Actin-based Motility, the Percentage of Moving Bacteria, and the Localization of Vasodilator-stimulated Phosphoprotein and Profilin," J. Cell. Biol., 135(3):647-660 (1996).

Southwick, F.S. and Purich, D.L., "Arrest of *Listeria* movement in host cells b a bacterial ActA analogue: Implications for actin-based motility," Proc. Natl. Acad. Sci. USA, 91:5168-5172 (1994).

Suarez, M., et al., "A role for ActA in epithelial cell invasion by *Listeria monocytogenes*," Cell Microbiol. 3(12):853-864 (2001).

Theriot, J.A., et al., "*Listeria Monocytogenes*-Based Assays for Actin Assembly Factors," Methods Enzymol. 298:114-122 (1998).

Tonan, K., et al., "Conformations of Isolated Fragments of Pancreatic Polypeptide," Biochemistry, 29:4424-4429 (1990).

Vita, C., et al., "Novel Miniproteins Engineered by the Transfer of Active Sites to Small Natural Scaffolds," Biopolymers, 47:93-100 (1998).

Vita, C., et al., "Scorpion toxins as natural scaffolds for protein engineering," Proc. Natl. Acad. Sci. USA, 92:6404-6408 (1995).

Williamson, M.P., "The structure and function of proline-rich regions in proteins," Biochem. J., 297:249-260 (1994).

Wills, Z., et al., "The Tyrosine Kinase Abl and Its Substrate Enabled Collaborate with the Receptor Phosphatase Dlar to Control Motor Axon Guidance," Neuron, 22:301-312 (1999).

Zarrinpar, A., et al., "The Structure and Function of Proline Recognition Domains," Sci. STKE RE8 (2003).

Zondlo, et al., "Highly Specific DNA Recognition by a Designed Miniature Protein", J. Am. Chem. Soc., 121:6938-6939 (1999).

```
         1    5      10        20      27
aPP     GPSQPTYPGDDAPVEDLIRFYNDLQQYLNVV
FP4        FPXΦP
ActA11     DFPPPPTDEEL
pGolemi    PFPPTPPGEEAPVEDLIRFYNDLQQYLNVV
PPII7      PFPPTPP
PPII11     PFPPTPPGEEA
```

E

```
F2A    PAPPTPPGEEAPVEDLIRFYNDLQQYLNVV
T5L    PFPPLPPGEEAPVEDLIRFYNDLQQYLNVV
F2L    PLPPTPPGEEAPVEDLIRFYNDLQQYLNVV
A11L   PFPPTPPGEELPVEDLIRFYNDLQQYLNVV
```

PROTEIN BINDING MINIATURE PROTEINS AND USES THEREOF

RELATED APPLICATIONS

This application claims the benefit of U.S. provisional application No. 60/529,401, filed Dec. 11, 2003, the disclosure of which is hereby incorporated by reference in its entirety.

FUNDING

Work described herein was funded, in part, by National Institutes of Health Grant GM 59843. The United States government has certain rights to the invention.

BACKGROUND

Biological interactions, such as protein:protein interactions, protein:nucleic acid interactions, and protein:ligand interactions are involved in a wide variety of processes occurring in living cells. For example, agonism and antagonism of receptors by specific ligands may effect a variety of biological processes such as gene expression, cellular differentiation and growth, enzyme activity, metabolite flow and metabolite partitioning between cellular compartments. Undesirable or inappropriate gene expression and/or cellular differentiation, cellular growth and metabolism may be attributable, at least in many cases, to biological interactions involving the binding and/or activity of proteinaceous molecules, such as transcription factors, peptide hormones, receptor molecules, and enzymes.

Peptides present potential therapeutic and prophylactic agents for many human and animal diseases, biochemical disorders and adverse drug effects, because they can interact highly specifically with other molecules. Thus, mimetic peptides have been designed and developed based on three dimensional protein structures. For example, many proteins recognize nucleic acids, other proteins or macromolecular assemblies using a partially exposed alpha helix. Within the context of a native protein fold, such alpha helices are usually stabilized by extensive tertiary interactions with residues that may be distant in primary sequence from both the alpha helix and from each other. With notable exceptions (Armstrong et al., 1993, *J. Mol. Biol.*, 230: 284-291), removal of these tertiary interactions destabilizes the alpha helix and results in molecules that neither fold nor function in macromolecular recognition (Zondlo et al., 1999, *J. Am. Chem. Soc.*, 121: 6938-6939). The ability to recapitulate or perhaps even improve on the recognition properties of an alpha helix within the context of a small molecule may find utility in the design of synthetic mimetics or inhibitors of protein function (Cunningham et al., 1997, *Curr. Opin. Struct. Biol.*, 7:457-462) or new tools for proteomics research.

Proteins generally recognize each other using large and shallow complementary surfaces. Therefore, small proteins (miniature proteins) with well-defined three-dimensional structures and finely tuned functional properties are perhaps ideally suited for protein surface recognition and disruption of protein:protein interaction. Clearly, there is a need for developing the miniature proteins (in particular, those with high affinity and high specificity for a target molecule) as therapeutics and prophylactics.

SUMMARY OF THE INVENTION

In certain embodiments, the invention relates to an avian pancreatic polypeptide (aPP) modified by substitution of at least one amino acid residue, which is located within (as a component of) a type II polyproline (PPII) helix of the polypeptide when the polypeptide is in a tertiary form. In some embodiments, the modified polypeptide contains at least two or three substituted residues. Optionally, the residue substitutions can include modification of position 2 (e.g., F in SEQ ID NO:1) with other hydrophobic residues (L, I, V, A). In other embodiments, the modified polypeptide is further modified by substitution of at least one amino acid residue (e.g., two residues) of the linker region between the PPII helix and the alpha helix domain of the polypeptide. The modified polypeptide of the invention is also referred to as a miniature protein.

In certain cases, the substituted residue of the PPII helix is selected from a site on a first protein through which the first protein interacts with a second protein. The first protein can be a known protein such as, but are not limited to, a protein that interacts with EVH1 domains. Examples of the first proteins include zyxin, vinculin, and the ActA protein of *Listeria monocytogenes*. The second protein which interacts with the first protein includes but is not limited to any protein that contains an EVH1. For example, the second protein can be selected from the group consisting of: *Drosophila* Enabled (Ena), mammalian Mena, vasodilator stimulated phosphoprotein (VASP), Enabled/VASP-like protein (Evl), and Wiskott-Aldrich syndrome protein (WASP). In a preferred embodiment, the site on the first protein is a protein binding site (e.g., a polyproline helix). In some embodiments, the modified avian pancreatic polypeptide is capable of inhibiting the interaction between the first protein and the second protein, while in other embodiments, it is capable of enhancing this interaction.

In a specific embodiment, the miniature protein of the invention preferentially binds to one protein selected from the group consisting of: *Drosophila* Enabled (Ena), mammalian Mena, vasodilator stimulated phosphoprotein (VASP), Enabled/VASP-like protein (Evl), and Wiskott-Aldrich syndrome protein (WASP), but does not bind to the other proteins of the group.

In certain embodiments, the invention encompasses a phage-display library comprising a plurality of recombinant phage that express any of the aforementioned modified avian pancreatic polypeptides. In a related embodiment, the invention encompasses a phage-display library comprising a plurality of recombinant phage that express a protein scaffold modified by substitution of at least one amino acid residue, this residue being exposed on a type II polyproline helix of the polypeptide when the polypeptide is in a tertiary form. In some cases, the protein scaffold of the phage-display library comprises the avian pancreatic polypeptide. The invention also encompasses an isolated phage selected from the phage library of the invention.

In a specific embodiment, a miniature protein of the invention comprises the amino acid sequence PFPPTPPGEEAPV-EDLIRFYNDLQQYLNVV (SEQ ID NO: 1). In other embodiments, the miniature protein may comprise any of the following amino acid sequence: PAPPTPPGEEAPVEDLIR-FYNDLQQYLNVV (SEQ ID NO: 2); PFPPLPPGEEAPV-EDLIRFYNDLQQYLNVV ((SEQ ID NO: 3); PLPPTPP-GEEAPVEDLIRFYNDLQQYLNVV (SEQ ID NO: 4); PFPPTPPGEELPVEDLIRFYNDLQQYLNVV (SEQ ID NO: 5). Further, the present invention contemplates all the variants with A substituted at each non-A position of the avian pancreatic polypeptide, and all the variants with sarcosine substituted at positions 1-8 of the avian pancreatic polypeptide.

Further, the present invention provides an isolated polypeptide selected from the group consisting of: (a) an isolated polypeptide comprising any of the amino acid sequences as set forth in SEQ ID NOs: 1-5; (b) an isolated polypeptide comprising a fragment of at least twelve contiguous amino acids of any of SEQ ID NOs: 1-5; (c) an isolated polypeptide comprising one or more amino acid substitutions in any of the amino acid sequences as set forth in SEQ ID NOs: 1-5; and (d) an isolated polypeptide at least 95 percent identical to any of SEQ ID NOs: 1-5.

In a related embodiment, the invention also encompasses a nucleic acid encoding any one of the aforementioned miniature polypeptides of the invention.

In certain embodiments, the invention encompasses a method of preparing a miniprotein that modulates the interaction between a first protein and a second protein, comprising the steps of: (a) identifying at least one amino acid residue that contributes to the binding between a first protein and a second protein; and (b) modifying an avian pancreatic polypeptide by substitution of said at least one amino acid residue, such that said at least one amino acid residue is exposed on a type II polyproline (PPII) helix of the polypeptide when the polypeptide is in a tertiary form. As used herein, the term “modulate” refers to an alteration (enhancement or inhibition) in the association between two molecular species, for example, the effectiveness of a biological agent to interact with its target by altering the characteristics of the interaction in a competitive or non-competitive manner.

In certain embodiments, the invention further encompasses a method of identifying a miniprotein that modulates the interaction between a first protein and a second protein, comprising a step of isolating at least one recombinant phage clone from the phage display library of the invention that displays a protein scaffold that modulates the association between a first protein and a second protein.

In certain embodiments, the invention provides a method of modulating (enhancing or inhibiting) cell migration, comprising contacting a cell with a modified polypeptide of the invention in an effective amount for modulating cell migration, wherein the modified polypeptide regulates signaling through a protein of the Ena/VASP family (an Ena/VASP protein). In this method, the Ena/VASP protein is preferably selected from the group consisting of: *Drosophila* Enabled (Ena), mammalian Mena, vasodilator stimulated phosphoprotein (VASP), Enabled/VASP-like protein (Evl), and Wiskott-Aldrich syndrome protein (WASP). Optionally, the modified polypeptide binds to an EVH1 domain of the Ena/VASP protein. A preferred cell of this method is a mammalian cell. In certain cases, the mammalian cell is a tumor cell.

In certain embodiments, the invention provides a method for inhibiting tumor cell metastasis in a subject, comprising administering to a subject having or at risk of developing a metastatic cancer a modified polypeptide of the invention in an effective amount for inhibiting cell migration such that tumor cell metastasis is inhibited, wherein the modified polypeptide inhibits signaling through an Ena/VASP protein. In this method, the Ena/VASP protein is preferably selected from the group consisting of: *Drosophila* Enabled (Ena), mammalian Mena, vasodilator stimulated phosphoprotein (VASP), Enabled/VASP-like protein (Evl), and Wiskott-Aldrich syndrome protein (WASP). Optionally, the modified polypeptide binds to an EVH1 domain of the Ena/VASP protein. A preferred subject of this method is a mammal, for example, a human.

In certain embodiments, the invention provides a method of modulating (enhancing or inhibiting) growth of a neuronal cell, comprising contacting a neuronal cell with a modified polypeptide of the invention in an effective amount for modulating growth of the neuronal cell, wherein the modified polypeptide regulates signaling through an Ena/VASP protein. In this method, the Ena/VASP protein is preferably selected from the group consisting of: *Drosophila* Enabled (Ena), mammalian Mena, vasodilator stimulated phosphoprotein (VASP), Enabled/VASP-like protein (Evl), and Wiskott-Aldrich syndrome protein (WASP). Optionally, the modified polypeptide binds to an EVH1 domain of the Ena/VASP protein.

In certain embodiments, the invention provides a method of inhibiting neurodegeneration in a subject, comprising administering to a subject at risk of a neurodegeneration disorder a modified polypeptide of the invention in an amount effective to prevent neurodegeneration, wherein the modified polypeptide regulates signaling through an Ena/VASP protein. In this method, the Ena/VASP protein is preferably selected from the group consisting of: *Drosophila* Enabled (Ena), mammalian Mena, vasodilator stimulated phosphoprotein (VASP), Enabled/VASP-like protein (Evl), and Wiskott-Aldrich syndrome protein (WASP). Optionally, the modified polypeptide binds to an EVH1 domain of the Ena/VASP protein. A variety of neurodegenerative disorders can be treated by this method, such as Down Syndrome; Parkinson’s disease; amyotrophic lateral sclerosis (ALS), stroke, direct trauma, Huntington’s disease, epilepsy, ALS-Parkinsonism-dementia complex; progressive supranuclear palsy; progressive bulbar palsy, spinomuscular atrophy, cerebral amyloidosis, Pick’s atrophy, Retts syndrome; Wilson’s disease, Striatonigral degeneration, corticobasal ganglionic degeneration; dentatorubral atrophy, olivopontocerebellar atrophy, paraneoplastic cerebellar degeneration; Tourettes syndrome, hypoglycemia; hypoxia; Creutzfeldt-Jakob disease; and Korsakoffs syndrome.

FIG. 1C is a spectra showing the mean residue ellipticity ($\Theta_{MRE}$) of 5 μM pGolemi at 25° C.

FIG. 1D shows the temperature dependence of the $\Theta_{MRE}$ at 222 nm.

FIG. 1E shows amino acid sequences of four additional miniature proteins of the invention.

FIGS. 2A-2D show interactions between EVH1 domains, miniature proteins and peptides measured by fluorescence perturbation (A, C, and D) or fluorescence polarization (B). FIG. 2A shows binding of pGolemi (magenta), $ActA_{11}$ (red) or PPII7 (yellow). FIGS. 2B and 2C show binding of $pGolemi^{Flu}$ (25 nM, B) or pGolemi (C) to $Mena_{1-112}$ (circle), $VASP_{1-115}$ (triangle) or $Evl_{1-115}$ (square). FIG. 1D shows binding of $ActA_{11}$ to $Mena_{1-112}$ (circle), $VASP_{1-115}$ (triangle) or $Evl_{1-115}$ (square). Fraction bound refers to fraction of EVH1 domain bound (A, C, D) or $pGolemi^{Flu}$ (B).

FIG. 3 shows median speed of *L. monocytogenes* observed in the absence (white) or presence of pgolemi (purple) and $ActA_{11}$ (red). Errors bars show the intraquartile range.

DETAILED DESCRIPTION OF THE INVENTION

Figure 1:
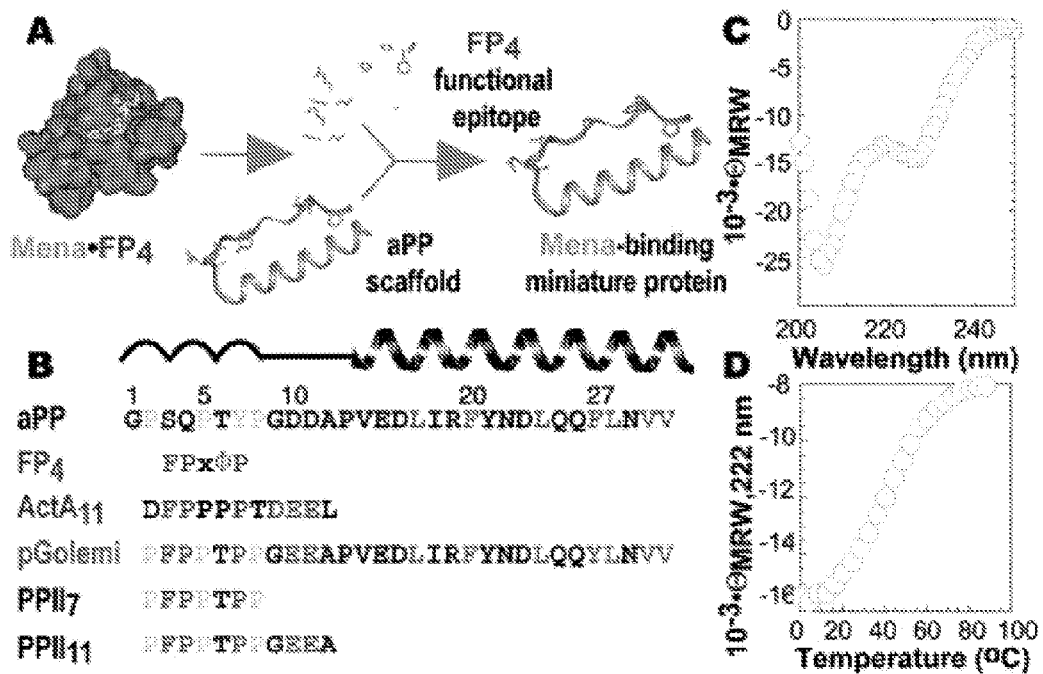
FIG. 1A shows protein grafting of the FP4 epitope on a miniature protein scaffold.

FIG. 1B shows sequences of peptides and miniature proteins described in this work. Residues important for aPP folding are in blue or yellow, residues important for $Mena_{1-112}$ recognition are in red. These amino acid residues are shown in duplicate in black font in the lower panel of FIG. 1B.

The present invention is based at least in part on protein grafting, an approach to protein minimization that was successfully developed by Applicants. The protein grafting approach has been used for the identification of highly functional miniature proteins by stabilization of α-helical binding epitopes on a protein scaffold (Zondlo et al., 1999, J. Am. Chem. Soc., 121:6938-6939; Chin et al., 2001, Bioorg. Med. Chem. Lett., 11:1501-1505; Chin et al., 2001, J. Am. Chem. Soc., 123:2929-2930; Chin et al., 2001, Angew Chem. Int. Ed. Engl., 2001, 40:3806-3809; Montclare et al., 2003, J. Am. Chem. Soc., 125:3416-3417; Rutledge et al., 2003, J. Am. Chem. Soc., 125:14336-47). In these methods, protein grafting involves removing residues required for molecular recognition from their native alpha helical context and grafting them on the scaffold provided by small yet stable proteins.

Numerous researchers have engineered protein scaffolds to present binding residues on a relatively small peptide carrier. These scaffolds are small polypeptides onto which residues critical for binding to a selected target can be grafted. The grafted residues are arranged in particular positions such that the spatial arrangement of these residues mimics that which is found in the native protein. These scaffolding systems are commonly referred to as miniproteins (miniature proteins). A common feature is that the binding residues are known before the miniprotein is constructed.

Examples of these miniproteins include the thirty-seven amino acid protein charybdotoxin (Vita et al., 1995, Proc. Natl. Acad. Sci. USA, 92: 6404-6408; Vita et al., 1998, Biopolymers, 47: 93-100) and the thirty-six amino acid protein, avian pancreatic peptide (Zondlo et al., 1999, Am. Chem. Soc., 121: 6938-6939). Avian pancreatic polypeptide (aPP) is a polypeptide in which residues fourteen through thirty-two form an alpha helix stabilized by hydrophobic contacts with an N-terminal type II polyproline (PPII) helix formed by residues one through eight. Because of its small size and stability, aPP is an excellent scaffold for protein grafting of alpha helical recognition epitopes (Zondlo et al., 1999, Am. Chem. Soc., 121: 6938-6939).

Miniature Proteins

The present invention provides engineered miniature proteins that associate with (bind to) specific sequences (DNA or other proteins) and also provides methods for designing and making these miniature proteins. As used herein, the term "miniature protein" or "miniprotein" refers to a relatively small protein containing at least a protein scaffold and one or more additional domains or regions that help to stabilize its tertiary structure. Preferably, these miniature proteins bind to a target molecule (e.g., DNA or other proteins) with high affinity and selectivity.

As used herein, the term "binding" or "bind to" refers to the specific association or other specific interaction between two molecular species, such as protein-protein interactions. It is contemplated that such association is mediated through specific binding sites on each of the two interacting molecular species. As used herein, the term "binding site" refers to the reactive region or domain of a molecule that directly participates in its specific binding with another molecule. For example, when referring to the binding site on a protein, binding occurs as a result of the presence of specific amino acid sequence that interacts with the other molecule.

Schematically, the invention involves a technique that the inventors have designated as protein grafting (see, e.g., FIG. 1). In one aspect, this technique identifies critical binding site residues from a protein that participate in binding-type association between that protein and its specific binding partners. Then these residues are grafted onto a small but stable protein scaffold. As used herein, the term "protein scaffold" refers to a region or domain of a relatively small protein, such as a miniature protein, that has a conserved tertiary structural motif which can be modified to display one or more specific amino acid residues in a fixed conformation. The preferred protein scaffolds of the invention comprise members of the pancreatic fold (PP fold) protein family, particularly the avian pancreatic polypeptide.

The PP fold protein scaffolds of the invention generally contain thirty-six amino acids and are the smallest known globular proteins. Despite their small size, PP fold proteins are stable and remain folded under physiological conditions. The preferred PP fold protein scaffolds of the invention consist of two anti-parallel helices, an N-terminal type II polyproline helix (PPII) between amino acid residues two and eight, and an alpha-helix between residues 14 and 31 and/or 32. The stability of the PP fold protein scaffolds of the invention derives predominantly from interactions between hydrophobic residues on the interior face of the alpha-helix at positions 17, 20, 24, 27, 28, 30, and 31 and the residues on the two edges of the polyproline helix at positions 2, 4, 5, 7, and 8. In general, the residues responsible for stabilizing its tertiary structure are not substituted in order to maintain the tertiary structure of the miniature protein or are compensated for using phage display.

In certain embodiments, at least one of the critical binding site residues of a selected protein is grafted onto the protein scaffold in positions which are not essential in maintaining tertiary structure, preferably on the type II polyproline helix. In one preferred embodiment, two or three of such binding site residues are grafted onto the protein scaffold (e.g., aPP). Preferred positions for grafting these binding site residues on the protein scaffold include, but are not limited to, positions on the type II polyproline helix of aPP. Substitutions of binding site residues may be made, although they are less preferred, for residues involved in stabilizing the tertiary structure of the miniature protein.

A skilled artisan will readily recognize that it is not necessary that actual substitution of the grafted residues occur on the protein scaffold. Rather it is necessary that a peptide be identified, through, for example, phage display, that comprises a polypeptide constituting a miniature protein having the association characteristics of the present invention. Such peptides may be produced using any conventional means, including, but not limited to synthetic and recombinant techniques.

Members of the PP fold family of protein scaffolds which are contemplated by the present invention include, but are not limited to, avian pancreatic polypeptide (aPP), Neuropeptide Y, lower intestinal hormone polypeptide, and pancreatic peptide. In the most preferred embodiment, the protein scaffold comprises the PP fold protein, avian pancreatic polypeptide (see, e.g., Blundell et al., 1981, Proc. Natl. Acad. Sci. USA, 78: 4175-4179; Tonan et al., 1990, Biochemistry, 29: 4424-4429). aPP is a PP fold polypeptide characterized by a short (eight residue) amino-terminal type II polyproline helix linked through a type I beta turn (also referred to herein as the linker region) to an eighteen residue alpha-helix. Because of its small size and stability, aPP is an excellent protein scaffold for, e.g., protein grafting of polyproline helix recognition epitopes.

In certain embodiments, the present invention encompasses miniature proteins that bind to a target protein. Optionally, the binding of the miniature proteins modulates protein-protein interaction between the target protein and its binding partner (protein). In one embodiment, making the protein-binding miniature proteins of the invention involves identifying the amino acid residues which are essential to binding of the target protein to its binding partner. In some embodiments, these essential residues are identified using three-dimensional models of a target protein or a protein complex which binds to or interacts with another protein based on crystallographic studies, while in other embodiments, they are identified by studies of deletion or substitution mutants of the target protein. The residues that participate in binding of the protein to its binding partner are then grafted onto those positions which are not necessary to maintain the tertiary structure of the protein scaffold to form the protein-binding miniature protein.

The structure of any protein which binds to another protein can be used to derive the protein-binding miniature proteins of the invention. Preferred embodiments include proline rich sequences on some proteins that are folded into type II polyproline (PPII) helices. The PPII helical structures can be recognized and bound to by certain protein motifs, such as EVH1 domains, SH3 domains, and WW domains.

In a specific embodiment, the invention provides miniature proteins that bind to a protein of the Ena/VASP family (herein referred to as "an Ena/VASP protein"). For example, the protein grafting procedure described herein was applied to the PPII helix of the ActA protein of *Listeria monocytogenes* to design a miniature protein capable of binding to an EnaN-ASP protein. In this procedure, the primary sequence of a PPII helix of a protein is aligned with residues in the PPII helix of aPP. Alignments with a large number of conflicts are eliminated as they would force selection between sequences that were well folded or have high affinity, but make it difficult to isolate a molecule with both these properties. Structural models of the aPP based peptides that are associated or complexed with the EVH1 domain of an Ena/VASP protein in each of the alignments are evaluated for unfavorable interactions or steric clashes between the VanderWaals surface of the Ena/VASP protein and the backbone of the aPP scaffold. Structural models with multiple unfavorable interactions or steric clashes are eliminated from further consideration.

Examples of the protein-binding miniature proteins which bind to an Ena/VASP protein include, but are not limited to, the amino acid sequence depicted in SEQ ID NOs: 1-5 (FIG. 1).

Variants of Miniature Proteins

The miniature proteins of the present invention further include conservative variants of the miniature proteins herein described. As used herein, a conservative variant refers to alterations in the amino acid sequence that do not substantially and adversely affect the binding or association capacity of the protein. A substitution, insertion or deletion is said to adversely affect the miniature protein when the altered sequence prevents or disrupts a function or activity associated with the protein. For example, the overall charge, structure or hydrophobic-hydrophilic properties of the miniature protein can be altered without adversely affecting an activity. Accordingly, the amino acid sequence can be altered, for example to render the peptide more hydrophobic or hydrophilic, without adversely affecting the activities of the miniature protein.

These variants, though possessing a slightly different amino acid sequence than those recited above, will still have the same or similar properties associated with the miniature proteins depicted in SEQ ID NOs: 1-5. Ordinarily, the conservative substitution variants, will have an amino acid sequence having at least ninety percent amino acid sequence identity with any of the miniature sequences set forth in SEQ ID NOs: 1-5, more preferably at least ninety-five percent, even more preferably at least ninety-eight percent, and most preferably at least ninety-nine percent. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. N-terminal, C-terminal or internal extensions, deletions, or insertions into the peptide sequence shall not be construed as affecting homology.

Thus, the miniature proteins of the present invention include molecules comprising any of the amino acid sequences of SEQ ID NOs: 1-5; fragments thereof having a consecutive sequence of at least about 20, 25, 30, 35 or more contiguous amino acid residues of the miniature proteins of the invention; amino acid sequence variants of such sequences wherein at least one amino acid residue has been inserted N- or C-terminal to, or within, the disclosed sequence; amino acid sequence variants of the disclosed sequences, or their fragments as defined above, that have been substituted by another residue. Contemplated variants further include those derivatives wherein the protein has been covalently modified by substitution, chemical, enzymatic, or other appropriate means with a moiety other than a naturally occurring amino acid (for example, a detectable moiety such as an enzyme or radioisotope).

Nucleic Acid Molecules Encoding Miniature Proteins

The present invention further provides nucleic acid molecules that encode the subject miniature proteins (e.g., comprising any of the amino acid sequences of SEQ ID NOs: 1-5) and the related miniature proteins herein described, preferably in isolated form. As used herein, "nucleic acid" includes cDNA and mRNA, as well as nucleic acids based on alternative backbones or including alternative bases whether derived from natural sources or synthesized. As used herein, a nucleic acid molecule is said to be "isolated" when the nucleic acid molecule is substantially separated from contaminant nucleic acid encoding other polypeptides from the source of nucleic acid.

The present invention further provides fragments of the encoding nucleic acid molecule. As used herein, a "fragment of an encoding nucleic acid molecule" refers to a portion of the entire protein encoding sequence of the miniature protein. The size of the fragment will be determined by the intended use. For example, if the fragment is chosen so as to encode an active portion of the protein, the fragment will need to be large enough to encode the functional region(s) of the protein. The appropriate size and extent of such fragments can be determined empirically by persons skilled in the art.

Modifications to the primary structure itself by deletion, addition, or alteration of the amino acids incorporated into the protein sequence during translation can be made without destroying the activity of the miniature protein. Such substitutions or other alterations result in miniature proteins having an amino acid sequence encoded by a nucleic acid falling within the contemplated scope of the present invention.

The present invention further provides recombinant DNA molecules that contain a coding sequence. As used herein, a recombinant DNA molecule is a DNA molecule that has been subjected to molecular manipulation. Methods for generating recombinant DNA molecules are well known in the art, for example, see Sambrook et al., (1989) Molecular Cloning—A Laboratory Manual, Cold Spring Harbor Laboratory Press. In the preferred recombinant DNA molecules, a coding DNA sequence is operably linked to expression control sequences and vector sequences.

The choice of vector and expression control sequences to which one of the protein family encoding sequences of the present invention is operably linked depends directly, as is well known in the art, on the functional properties desired (e.g., protein expression, and the host cell to be transformed). A vector of the present invention may be at least capable of directing the replication or insertion into the host chromosome, and preferably also expression, of the structural gene included in the recombinant DNA molecule.

Expression control elements that are used for regulating the expression of an operably linked miniature protein encoding sequence are known in the art and include, but are not limited to, inducible promoters, constitutive promoters, secretion signals, and other regulatory elements. Preferably, the inducible promoter is readily controlled, such as being responsive to a nutrient in the host cell's medium.

In one embodiment, the vector containing a coding nucleic acid molecule will include a prokaryotic replicon, i.e., a DNA sequence having the ability to direct autonomous replication and maintenance of the recombinant DNA molecule extra-chromosomal in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical of bacterial drug resistance genes are those that confer resistance to ampicillin or tetracycline.

Vectors that include a prokaryotic replicon can further include a prokaryotic or bacteriophage promoter capable of directing the expression (transcription and translation) of the coding gene sequences in a bacterial host cell, such as E. coli. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Any suitable prokaryotic host can be used to express a recombinant DNA molecule encoding a protein of the invention.

Expression vectors compatible with eukaryotic cells, preferably those compatible with vertebrate cells, can also be used to form a recombinant DNA molecules that contains a coding sequence. Eukaryotic cell expression vectors are well known in the art and are available from several commercial sources. Typically, such vectors are provided containing convenient restriction sites for insertion of the desired DNA segment.

Eukaryotic cell expression vectors used to construct the recombinant DNA molecules of the present invention may further include a selectable marker that is effective in an eukaryotic cell, preferably a drug resistance selection marker. A preferred drug resistance marker is the gene whose expression results in neomycin resistance, i.e., the neomycin phosphotransferase (neo) gene. (Southern et al., (1982) J. Mol. Anal. Genet. 1, 327-341). Alternatively, the selectable marker can be present on a separate plasmid, the two vectors introduced by co-transfection of the host cell, and transfectants selected by culturing in the appropriate drug for the selectable marker.

Transformed Host Cells

The present invention further provides host cells transformed with a nucleic acid molecule that encodes a miniature protein of the present invention. The host cell can be either prokaryotic or eukaryotic. Eukaryotic cells useful for expression of a miniature protein of the invention are not limited, so long as the cell line is compatible with cell culture methods and compatible with the propagation of the expression vector and expression of the gene product.

Transformation of appropriate cell hosts with a recombinant DNA molecule encoding a miniature protein of the present invention is accomplished by well known methods that typically depend on the type of vector used and host system employed. With regard to transformation of prokaryotic host cells, electroporation and salt treatment methods can be employed (see, for example, Sambrook et al., (1989) Molecular Cloning—A Laboratory Manual, Cold Spring Harbor Laboratory Press; Cohen et al., (1972) Proc. Natl. Acad. Sci. USA 69, 2110-2114). With regard to transformation of vertebrate cells with vectors containing recombinant DNA, electroporation, cationic lipid or salt treatment methods can be employed (see, for example, Graham et al., (1973) Virology 52, 456-467; Wigler et al., (1979) Proc. Natl. Acad. Sci. USA 76, 1373-1376).

Successfully transformed cells (cells that contain a recombinant DNA molecule of the present invention), can be identified by well known techniques including the selection for a selectable marker. For example, cells resulting from the introduction of a recombinant DNA of the present invention can be cloned to produce single colonies. Cells from those colonies can be harvested, lysed and their DNA content examined for the presence of the recombinant DNA using a method such as that described by Southern, (1975) J. Mol. Biol. 98, 503-517 or the proteins produced from the cell assayed via an immunological method.

Production of Recombinant Miniature Proteins

The present invention further provides methods for producing a miniature protein of the invention using nucleic acid molecules herein described. In general terms, the production of a recombinant form of a protein typically involves the following steps: a nucleic acid molecule is obtained that encodes a miniature protein of the invention, for example, the nucleic acid molecule encoding the miniature protein depicted in any of SEQ ID NOs: 1-5. The nucleic acid molecule is then preferably placed in operable linkage with suitable control sequences, as described above, to form an expression unit containing the protein open reading frame. The expression unit is used to transform a suitable host and the transformed host is cultured under conditions that allow the production of the recombinant miniature protein. Optionally the recombinant miniature protein is isolated from the medium or from the cells; recovery and purification of the protein may not be necessary in some instances where some impurities may be tolerated.

Each of the foregoing steps can be done in a variety of ways. The construction of expression vectors that are operable in a variety of hosts is accomplished using appropriate replicons and control sequences, as set forth above. The control sequences, expression vectors, and transformation methods are dependent on the type of host cell used to express the gene. Suitable restriction sites, if not normally available, can be added to the ends of the coding sequence so as to provide an excisable gene to insert into these vectors. A skilled artisan can readily adapt any host/expression system known in the art for use with the nucleic acid molecules of the invention to produce a recombinant miniature protein.

The present invention further contemplates making the miniature proteins by chemical synthesis.

Production of Miniature Proteins Using Phage Display

In some embodiments, the present invention contemplates producing and selecting a miniature protein using a phage display method (McCafferty et al., (1990) Nature 348, 552-554). In this method, display of recombinant miniature proteins on the surface of viruses which infect bacteria (bacteriophage or phage) make it possible to produce soluble, recombinant miniature proteins having a wide range of affinities and kinetic characteristics. To display the miniature proteins on the surface of phage, a synthetic gene encoding the miniature protein is inserted into the gene encoding a phage surface protein (e.g., pIII) and the recombinant fusion protein is expressed on the phage surface (McCafferty et al., 1990, Nature, 348: 552-554; Hoogenboom et al., 1991, Nucleic Acids Res., 19: 4133-4137). Variability is introduced into the phage display library to select for miniature proteins which not only maintain their tertiary, helical structure but which also display increased affinity for a preselected target because the critical (or contributing but not critical) binding residues are optimally positioned on the helical structure.

Since the recombinant proteins on the surface of the phage are functional, phage bearing miniature proteins that bind with high-affinity to a particular target molecule (e.g., a protein) can be separated from non-binding or lower affinity phage by antigen affinity chromatography. Mixtures of phage are allowed to bind to the affinity matrix, non-binding or lower affinity phage are removed by washing, and bound phage are eluted by treatment with acid or alkali. Depending on the affinity of the miniature protein for its target, enrichment factors of twenty-fold to a million-fold are obtained by a single round of affinity selection. By infecting bacteria with the eluted phage, however, more phage can be grown and subjected to another round of selection. In this way, an enrichment of a thousand-fold in one round becomes a million-fold in two rounds of selection. Thus, even when enrichments in each round are low (Marks et al., 1991, J. Mol. Biol, 222: 581-597), multiple rounds of affinity selection leads to the isolation of rare phage and the genetic material contained within which encodes the sequence of the domain or motif of the recombinant miniature protein that binds or otherwise specifically associates with it binding target.

In various embodiments of the invention, the methods disclosed herein are used to produce a phage expression library encoding miniature proteins capable of binding to protein that has already been selected using the protein grafting procedure described above. In these embodiments, phage display can be used to identify miniature proteins that display an even higher affinity for a particular target protein than that of the miniature proteins produced without the aid of phage display. In yet another embodiment, the invention encompasses a universal phage display library that can be designed to display a combinatorial set of epitopes or binding sequences to permit the recognition of target molecules (e.g., nucleic acids, proteins or small molecules) by a miniature protein without prior knowledge of the natural epitope or specific binding residues or motifs natively used for recognition and association.

Various structural modifications are also contemplated for the present invention that include the addition of restriction enzyme recognition sites into the polynucleotide sequence encoding the miniature protein that enable genetic manipulation of these gene sequences. Accordingly, the re-engineered miniature proteins can be ligated, for example, into an M13-derived bacteriophage cloning vector that permits expression of a fusion protein on the phage surface. These methods allow for selecting phage clones encoding fusion proteins that bind to a target molecule and can be completed in a rapid manner allowing for high-throughput screening of miniature proteins to identify the miniature protein with the highest affinity and selectivity for a particular target.

According to the methods of the invention, a library of phage displaying modified miniature proteins is incubated with the immobilized target molecule (e.g., a Mena protein) to select phage clones encoding miniature proteins that specifically bind to or otherwise specifically associate with the immobilized protein. This procedure involves immobilizing a polypeptide sample on a solid substrate. The bound phage are then dissociated from the immobilized polypeptide and amplified by growth in bacterial host cells. Individual viral plaques, each expressing a different recombinant miniature protein, are expanded to produce amounts of protein sufficient to perform a binding assay. The DNA encoding this recombinant binding protein can be subsequently modified for ligation into a eukaryotic protein expression vector. The modified miniature protein, adapted for expression in eukaryotic cells, is ligated into a eukaryotic protein expression vector.

Phage display methods that can be used to make the miniature proteins of the present invention include those disclosed in Brinkman et al., (1995) J. Immunol. Methods 182, 41-50; Ames et al., (1995) J. Immunol. Methods 184:177-186; Kettleborough et al., (1994) Eur. J. Immunol. 24, 952-958; Persic et al., (1997) Gene 187, 9-18; Burton et al., (1994) Adv. Immunol. 57, 191-280; U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743, 5,837,500 & 5,969,108.

Methods to Identify Binding Partners

In certain embodiments, the present invention relates to methods for use in isolating and identifying binding partners of the miniature proteins of the invention. In some aspects, a miniature protein of the invention is mixed with a potential binding partner or an extract or fraction of a cell under conditions that allow the association of potential binding partners with the miniature protein of the invention. After mixing, peptides, polypeptides, proteins or other molecules that have become associated with a miniature protein of the invention are separated from the mixture. The binding partner bound to the protein of the invention can then be removed and further analyzed. To identify and isolate a binding partner, the entire miniature protein can be used. Alternatively, a fragment of the miniature protein which contains the binding domain can be used.

As used herein, a "cellular extract" refers to a preparation or fraction which is made from a lysed or disrupted cell. A variety of methods can be used to obtain an extract of a cell. Cells can be disrupted using either physical or chemical disruption methods. Examples of physical disruption methods include, but are not limited to, sonication and mechanical shearing. Examples of chemical lysis methods include, but are not limited to, detergent lysis and enzyme lysis. A skilled artisan can readily adapt methods for preparing cellular extracts in order to obtain extracts for use in the present methods. Once an extract of a cell is prepared, the extract is mixed with a miniature protein of the invention under conditions in which association of the miniature protein with the binding partner can occur. A variety of conditions can be used, the most preferred being conditions that closely resemble conditions found in the cytoplasm of a human cell. Features such as osmolarity, pH, temperature, and the concentration of cellular extract used, can be varied to optimize the association of the protein with the binding partner.

After mixing under appropriate conditions, the bound complex is separated from the mixture. A variety of techniques can be utilized to separate the mixture. For example, antibodies specific to a protein of the invention can be used to immunoprecipitate the binding partner complex. Alternatively, standard chemical separation techniques such as chromatography and density-sediment centrifugation can be used. After removal of non-associated cellular constituents found in the extract, the binding partner can be dissociated from the complex using conventional methods. For example, dissociation can be accomplished by altering the salt concentration or pH of the mixture.

To aid in separating associated binding partner pairs from the mixed extract, the miniature protein of the invention can be immobilized on a solid support. For example, the miniature protein can be attached to a nitrocellulose matrix or acrylic beads. Attachment of the miniature protein to a solid support aids in separating peptide-binding partner pairs from other constituents found in the extract. The identified binding partners can be either a single protein or a complex made up of two or more proteins. Alternatively, binding partners may be identified using the Alkaline Phosphatase fusion assay according to the procedures of Flanagan & Vanderhaeghen, (1998) Annu. Rev. Neurosci. 21, 309-345 or Takahashi et al., (1999) Cell 99, 59-69; the Far-Western assay according to the procedures of Takayama et al., (1997) Methods Mol. Biol. 69, 171-184 or Sauder et al., J. Gen. Virol. (1996) 77, 991-996 or identified through the use of epitope tagged proteins or GST fusion proteins.

Alternatively, the nucleic acid molecules encoding a miniature protein of the invention can be used in a yeast two-hybrid system. The yeast two-hybrid system has been used to identify other protein partner pairs and can readily be adapted to employ the nucleic acid molecules herein described (see, e.g., Stratagene Hybrizap® two-hybrid system).

EVH1 Domains and Ena/VASP Protein Family

In certain embodiments, miniature proteins of the invention binds to an Ena/VASP protein with high affinity and high specificity. The evolutionarily-conserved Ena/VASP protein family has been implicated in the regulation of cell migration (Gertler et al., 1996, Cell, 87: 227-39). Enabled (Ena) was identified as a genetic suppressor of loss-of-function mutations in Drosophila Ableson tyrosine kinase (D-Ab1) (Gertler et al., 1990, Science, 248: 857-60). Loss-of-function mutations in Ena ameliorated the embryonic central nervous system defects associated with loss of D-Ab1 in combination with mutations in any of several known D-Ab1 modifier genes (Gertler, et al., 1995, Genes Dev, 9: 521-33). VASP was identified biochemically as an abundant substrate for cyclic-nucleotide dependent kinases in mammalian platelets (Halbrugge et al., 1990, J Chromatogr, 521: 335-43). Two other mammalian members of this protein family, Mena (mammalian Enabled) and EVL (Ena/VASP like), were identified by sequence similarity (Gertler et al., 1996, Cell, 87: 227-39).

All Ena/VASP family members share a conserved domain structure. The N-terminal third of the protein, called the EVH1 (Ena VASP Homology) domain, mediates subcellular targeting of Ena/VASP proteins to focal adhesions by binding to proteins containing a motif whose consensus is D/E FPP-PPX D/E (Niebuhr et al., 1997, Embo J, 16: 5433-44). Mutational analysis indicated that the phenylalanine residue, along with flanking acidic residues on either side, are critical for optimal binding (Carl et al., 1999, Curr Biol, 9: 715-8). The EVH1 ligand motif is found in a number of cellular proteins, including the focal adhesion proteins zyxin and vinculin. The central portion of Ena/VASP proteins contains proline-rich stretches, which have been reported to be binding sites for three types of proteins: the G-actin binding protein profilin, SH3 domain-containing proteins, and WW domain-containing proteins (Ermekova et al., 1997, J Biol Chem, 272: 32869-77; Gertler et al., 1996, Cell, 87: 227-39). The C-terminal third of Ena/VASP proteins contains the EVH2 domain that binds in vitro to F-actin and has a putative coiled-coil region reported to be important for multimerization (Bachmann et al., 1999, J Biol Chem, 274: 23549-57; Huttelmaier et al., 1999, FEBS Lett, 451: 68-74).

In addition to their capacity to bind profilin and actin, the localization of Ena/VASP proteins suggests that they may be involved in regulating actin dynamics and/or adhesion (Reinhard et al., 1992, Embo J., 11: 2063-70; Gertler et al., 1996, Cell, 87: 227-39; Lanier et al., 1999, Neuron, 22: 313-25). Genetic analyses of Ena/VASP family members in flies and mice demonstrated that these proteins function in processes that involve cell shape change, and movement including platelet aggregation and axon guidance (Aszodi et al., 1999, Embo J., 18: 37-48; Wills et al., 1999, Neuron, 22: 301-12).

Ena/VASP proteins are also implicated in actin dynamics by their role in facilitating the actin-based motility of the intracellular bacterial pathogen *Listeria monocytogenes*. The *Listeria* protein, ActA is required for the formation of actin tails characteristic of motile bacteria (Kocks et al., 1992, Cell, 68: 521-31). Furthermore, the motility of the intracellular pathogen *Listeria monocytogenes* resulting from rapid actin polymerization at one pole of the bacterium requires Ena (Laurent et al., 1999, J. Cell Biol, 144: 1245-58; Loisel et al., 1999, Nature 401, 613-6). ActA is a multi-domain protein on the surface of the bacteria that interacts with host cell factors to trigger actin assembly (Pistor et al., 1995, Curr Biol 5: 517-25). Ena/VASP proteins are the only host cell factors known to bind directly to ActA in vivo, which contains four optimized copies of the D/E FPPPPXDDE EVH1 ligand motif (Niebuhr et al., 1997, Embo J., 16: 5433-44). Mutation of these repeats leads to a defect in bacterial movement, despite the fact that an actin cloud and short actin tails still form around the bacterium (Smith et al., 1996, J. Cell Bio. 135:647-660; Niebuhr et al., 1997, Embo J, 16: 5433-44).

Therapeutic Uses

The discovery that miniature proteins of the invention display high affinity for a natural ActA target (e.g., an Ena/VASP protein) and show paralog specificity suggests that miniature proteins can modulate mammalian cell migration. Therefore, these miniature proteins can be important therapeutic compounds for diseases such as cancer cell metastasis, immune regulation, inflammatory disease, and neurodegenerative disorders.

In some aspects of the invention, miniature proteins of the invention are administrated to a subject in an effective amount to inhibit (completely or partially) migration of a tumor cell across a barrier. The invasion and metastasis of cancer is a complex process which involves changes in cell adhesion properties which allow a transformed cell to invade and migrate through the extracellular matrix (ECM) and acquire anchorage-independent growth properties. Some of these changes occur at focal adhesions, which are cell/ECM contact points containing membrane-associated, cytoskeletal, and intracellular signaling molecules. Metastatic disease occurs when the disseminated foci of tumor cells seed a tissue which supports their growth and propagation, and this secondary spread of tumor cells is responsible for the morbidity and mortality associated with the majority of cancers. Thus the term "metastasis" as used herein refers to the invasion and migration of tumor cells away from the primary tumor site.

Miniature proteins of the invention are also useful for treating and/or preventing disorders associated with inflammation in a subject. For example, when an Ena/VASP protein activity is induced in immune or hematopoetic cells, the ability of the cells to migrate is reduced. Thus, the subject minature proteins can induce activity of an Ena/VASP protein in immune cells such that inflammatory disorders and ischemic diseases are prevented or treated.

Inflammatory disorders and ischemic diseases are characterized by inflammation associated with neutrophil migration to local tissue regions that have been damaged or have otherwise induced neutrophil migration and activation. While not intending to be bound by any particular theory, it is believed that excessive accumulation of neutrophils resulting from neutrophil migration to the site of injury, causes the release toxic factors that damage surrounding tissue. When the inflammatory disease is an acute stroke a tissue which is often damaged by neutrophil stimulation is the brain. As the active neutrophils accumulate in the brain an infarct develops.

An "inflammatory disease or condition" as used herein refers to any condition characterized by local inflammation at a site of injury or infection and includes autoimmune diseases, certain forms of infectious inflammatory states, undesirable neutrophil activity characteristic of organ transplants or other implants and virtually any other condition characterized by unwanted neutrophil accumulation at a local tissue site. These conditions include but are not limited to meningitis, cerebral edema, arthritis, nephritis, adult respiratory distress syndrome, pancreatitis, myositis, neuritis, connective tissue diseases, phlebitis, arteritis, vasculitis, allergy, anaphylaxis, ehrlichiosis, gout, organ transplants and/or ulcerative colitis.

An "ischemic disease or condition" as used herein refers to a condition characterized by local inflammation resulting from an interruption in the blood supply to a tissue due to a blockage or hemorrhage of the blood vessel responsible for supplying blood to the tissue such as is seen for myocardial or cerebral infarction. A cerebral ischemic attack or cerebral ischemia is a form of ischemic condition in which the blood supply to the brain is blocked. This interruption in the blood supply to the brain may result from a variety of causes, including an intrinsic blockage or occlusion of the blood vessel itself, a remotely originated source of occlusion, decreased perfusion pressure or increased blood viscosity resulting in inadequate cerebral blood flow, or a ruptured blood vessel in the subarachnoid space or intracerebral tissue.

The methods of the invention are also useful for treating cerebral ischemia. Cerebral ischemia may result in either transient or permanent deficits and the seriousness of the neurological damage in a patient who has experienced cerebral ischemia depends on the intensity and duration of the ischemic event. A transient ischemic attack is one in which the blood flow to the brain is interrupted only briefly and causes temporary neurological deficits, which often are clear in less than 24 hours. Permanent cerebral ischemic attacks, also called stroke, are caused by a longer interruption in blood flow to the brain resulting from either a thromboembolism or hemorrhage. A stroke causes a loss of neurons typically resulting in a neurologic deficit that may improve but that does not entirely resolve.

It has been discovered that mammalian cell migration can be induced by depleting the cell of functional Ena/VASP protein. Therefore, miniature proteins of the invention can be useful for regeneration of tissue, including wound healing and neuroregeneration, or prevention or treatment of neurodegenerative disease.

A "wound" as used herein, means a trauma to any of the tissues of the body, especially that caused by physical means. The wound healing process involves a complex cascade of biochemical and cellular events to restore tissue integrity following an injury. The wound healing process is typically characterized by four stages: 1) hemostasis; 2) inflammation; 3) proliferation; and 4) remodeling. The miniature proteins of the invention are useful for promoting wound healing by promoting cellular migration and thus remodeling. In one aspect, the methods of the invention are useful for treating a wound to the dermis or epidermis, e.g., a bum or tissue transplant, injury to the skin. Further, the methods of the invention may be used in the process of wound healing as well as tissue generation. When the methods of the invention are used to promote wound healing, cells may be manipulated to alter Ena/VASP activity in vitro and then added to the site of the wound or alternatively the cells present at the site of the wound may be manipulated in vivo to alter the activity of the Ena/VASP proteins in order to promote cellular movement. When the methods are used to promote tissue generation, cells can be manipulated and grown in vitro on a scaffold and then implanted into the body or alternatively the scaffold may be implanted in the body, or it may be a naturally occurring scaffold and cells manipulated in vivo or in vitro can be used to generate the tissue.

Another aspect of the invention involves methods for tissue regeneration, which are particularly applicable to growth of neuronal cells. Thus, the invention contemplates the treatment of subjects having or at risk of developing neurodegenerative disease in order to cause neuroregeneration. Neuronal cells include both central nervous system (CNS) neurons and peripheral nervous system (PNS) neurons. There are many different neuronal cell types. Examples include, but are not limited to, sensory and sympathetic neurons, cholinergic neurons, dorsal root ganglion neurons, and proprioceptive neurons (in the trigeminal mesencephalic nucleus), ciliary ganglion neurons (in the parasympathetic nervous system). A person of ordinary skill in the art will be able to easily identify neuronal cells and distinguish them from non-neuronal cells such as glial cells, typically utilizing cell-morphological characteristics, expression of cell-specific markers, and secretion of certain molecules.

"Neurodegenerative disorder" is defined herein as a disorder in which progressive loss of neurons occurs either in the peripheral nervous system or in the central nervous system. Examples of neurodegenerative disorders include: (i) chronic neurodegenerative diseases such as familial and sporadic amyotrophic lateral sclerosis (FALS and ALS, respectively), familial and sporadic Parkinson's disease, Huntington's disease, familial and sporadic Alzheimer's disease, multiple sclerosis, olivopontocerebellar atrophy, multiple system atrophy, progressive supranuclear palsy, diffuse Lewy body disease, corticodentatonigral degeneration, progressive familial myoclonic epilepsy, strionigral degeneration, torsion dystonia, familial tremor, Down's Syndrome, Gilles de la Tourette syndrome, Hallervorden-Spatz disease, diabetic peripheral neuropathy, dementia pugilistica, AIDS Dementia, age related dementia, age associated memory impairment, and amyloidosis-related neurodegenerative diseases such as those caused by the prion protein (PrP) which is associated with transmissible spongiform encephalopathy (Creutzfeldt-Jakob disease, Gerstmann-Straussler-Scheinker syndrome, scrapie, and kuru), and those caused by excess cystatin C accumulation (hereditary cystatin C angiopathy); and (ii) acute neurodegenerative disorders such as traumatic brain injury (e.g., surgery-related brain injury), cerebral edema, peripheral nerve damage, spinal cord injury, Leigh's disease, Guillain-Barre syndrome, lysosomal storage disorders such as lipofuscinosis, Alper's disease, vertigo as result of CNS degeneration; pathologies arising with chronic alcohol or drug abuse including, for example, the degeneration of neurons in locus coeruleus and cerebellum; pathologies arising with aging including degeneration of cerebellar neurons and cortical neurons leading to cognitive and motor impairments; and pathologies arising with chronic amphetamine abuse including degeneration of basal ganglia neurons leading to motor impairments; pathological changes resulting from focal trauma such as stroke, focal ischemia, vascular insufficiency, hypoxic-ischemic encephalopathy, hyperglycemia, hypoglycemia or direct trauma; pathologies arising as a negative side-effect of therapeutic drugs and treatments (e.g., degeneration of cingulate and entorhinal cortex neurons in response to anticonvulsant doses of antagonists of the NMDA class of glutamate receptor). and Wernicke-Korsakoff's related dementia. Neurodegenerative diseases affecting sensory neurons include Friedreich's ataxia, diabetes, peripheral neuropathy, and retinal neuronal degeneration. Neurodegenerative diseases of limbic and cortical systems include cerebral amyloidosis, Pick's atrophy, and Retts syndrome. The foregoing examples are not meant to be comprehensive but serve merely as an illustration of the term "neurodegenerative disorder."

Miniature proteins of the invention may be administrated to cells of a subject to treat or prevent diseases (e.g., cancer metastasis or inflammatory disorders) alone or in combination with the administration of other therapeutic compounds for the treatment or prevention of these disorders.

Diagnostic Uses

In certain embodiments, miniature proteins of the invention are useful for diagnostic purposes to identify the presence and/or detect the levels of a target protein that binds to the miniature proteins of the invention. For example, miniature proteins of the invention can be used to detect the levels of an Ena/VASP protein due to its high affinity and high specifity. Miniature proteins of this method can be labeled with a detectable marker. A wide range of detectable markers can be used, including but not limited to biotin, a fluorogen, an enzyme, an epitope, a chromogen, or a radionuclide. The method for detecting the label will depend on the nature of the label and can be any known in the art, e.g., film to detect a radionuclide; an enzyme substrate that gives rise to a detectable signal to detect the presence of an enzyme; antibody to detect the presence of an epitope, etc.

In a specific diagnostic embodiment, miniature proteins of the invention are included in a kit used to detect the presence of a particular protein (e.g., an Ena/VASP protein) in a biological sample.

Pharmaceutical Compositions.

In certain embodiments, therapeutic compounds of the present invention (e.g., miniature proteins) are formulated with a pharmaceutically acceptable carrier. Miniature proteins of the present invention can be administered alone or as a component of a pharmaceutical formulation (composition). The compounds may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the miniature proteins include those suitable for oral/nasal, topical, parenteral and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

Methods of preparing these formulations or compositions include combining one compound and a carrier and, optionally, one or more accessory ingredients. In general, the formulations are prepared by combining a compound with a liquid carrier, or a finely divided solid carrier, or both, and then, if necessary, shaping the product.

Formulations of the miniature proteins suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound as an active ingredient. A compound may also be administered as a bolus, electuary or paste.

In solid dosage forms for oral administration (capsules, tablets, pills, dragees, powders, granules, and the like), a miniature protein is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration of a miniature protein include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds (e.g., miniature proteins), may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

Methods of the invention can be administered topically, either to skin or to mucosal membranes (e.g., those on the cervix and vagina). This offers the greatest opportunity for direct delivery to tumor with the lowest chance of inducing side effects. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

Dosage forms for the topical or transdermal administration of a compound (e.g., a miniature protein) include powders, sprays, ointments, pastes, creams, lotions, gels, solutions, patches, and inhalants. The active compound may be mixed under sterile conditions with a pharmaceutically acceptable carrier, and with any preservatives, buffers, or propellants which may be required. The ointments, pastes, creams and gels may contain, in addition to a therapeutic compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

Pharmaceutical compositions suitable for parenteral administration may comprise one or more compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Injectable depot forms are made by forming microencapsule matrices of the compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

Formulations of the compounds for intravaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound. Optionally, such formulations suitable for vaginal administration also include pessaries, tampons, creams, gels, pastes, foams or spray formulations containing such carriers as are known in the art to be appropriate.

Exemplification

The invention now being generally described, it will be more readily understood by reference to the following examples, which are included merely for purposes of illustration of certain embodiments and embodiments of the present invention, and are not intended to limit the invention.

Introduction

EVH1 domains are found within a large number of multi-domain signaling proteins that regulate the dynamics of the actin cytoskeleton, including those where external stimuli regulate cellular motility, shape, and adhesion (1). Examples include *Drosophilia* Enabled (Ena) (2) and its mammalian counterparts Mena (1a), vasodilator-stimulated phosphoprotein (VASP) (3), Enabled/VASP-like protein (Evl) (1a), and Wiskott-Aldrich syndrome protein (WASP) (4). EVH1 domains regulate actin filiment dynamics through interactions with cytoskeleton-associated proteins including vinculin and zyxin, and are used by the ActA protein of *Listeria monocytogenes* during pathogenesis (5). Like SH3 and WW domains, EVH1 domains recognize proline-rich sequences on target proteins (6) that re folded into type II polyproline (PPII) helices (7). In the case of *L. monocytogenes*, the interaction of intracellular EVH1 domains with ActA contribute to the propulsion of the bacterium through the host cell cytoplasm and into neighboring cells (8).

Results

Previously, we have described a miniature protein design strategy in which the well-folded helix in avian pancreatic polypeptide (aPP) presents short α-helical recognition epitopes (FIG. 1A) (10, 11). The miniature proteins so designed recognize even shallow clefts on protein surfaces with nanomolar affinities and high specificity (11). aPP consists of an eight-residue PPII helix linked through a type I β-turn to a 20 residue α-helix. Here we extend this protein design strategy to stabilize the functional epitope of ActA on the PPII helix of aPP. Like miniature proteins that use an α-helix for protein recognition, the miniature protein designed in this way displays high affinity for the $Mena_{1-112}$ EVH1 domain and achieves the elusive goal of paralog specificity (12) discriminating well between EVH1 domains of $Mena_{1-112}$, $VASP_{1-115}$ and $Evl_{1-112}$.

Our design began with the structure of $Mena_{1-112}$ in complex with the proline-rich peptide $F_1P_2PP_4P_5$ ($FP_4$) (13). The structure shows the pentapeptide bound as a type II polyproline helix, with residues $P_2$, $P_4$ and $P_5$ nestled into the concave, V-shaped, binding surface on $Mena_{1-112}$, and residue $F_1$ anchoring the peptide in the N to C direction (13). Substitution of $FP_4$ residues $F_1$, $P_2$, and $P_5$ at positions $S_3$, $Q_4$, and $Y_7$ and aPP, and extension of this core sequence by two of three C-terminal acidic residues shown to improve affinity and specificity (13, 14, 5c) led to the final sequence of pGolemi (FIG. 1B).

pGolemi was synthesized using standard solid phase methods (9) and examined by circular dichroism (CD) spectroscopy (FIG. 1C). The CD spectrum of pGolemi at 25° C.

exhibited minima at 208 and 222 nm, as expected for a protein containing one or more α-helices, and was independent of concentration between 5 and 20 µM. The mean residue ellipticity ($\Theta_{MRE}$) at 222 nm of −5,500 deg·cm²·dmol⁻¹ suggests that approximately 60% of pGolemi possessed an α-helical conformation. The stability of pGolemi was examined further by monitoring the temperature-dependence of $\Theta_{MRE}$ at 222 nm. pGolemi underwent a reversible, moderately cooperative melting transition with $T_m$=50° C. (FIG. 1D). These data suggest that pGolemi adopts a stable, folded, monomeric, aPP-like structure.

The affinity and specificity of pGolemi-EVH1 domain interactions were measured by tryptophan perturbations analysis (FIG. 2A) (13). An 11 residue peptide comprising PPII repeat 2 of *L. monocytogenenes* ActA ($ActA_{11}$) and two peptides comprising the N-terminal 7 or 11 residues in pGolemi ($PPII_7$ and $PPII_{11}$) were prepared as controls. pGolemi bound $Mena_{1-112}$ with high affinity ($K_d$=700±30 nM) (9). This affinity is 10-fold higher than that of $ActA_{11}$, the best previously known Mena ligand (13). The interaction between pGolemi and $Mena_{1-112}$ was confirmed by fluorescence polarization experiments using a fluorescent pGolemi derivative ($pGolemi^{Flu}$) (FIG. 2B); the $K_d$ determined this way was 290±50 nM. Furthermore, pGolemi and $ActA_{11}$ compete with $pGolemi^{Flu}$ for binding to $Mena_{1-112}$ with $IC_{50}$ values of 542±30 nM and 4.0±0.2 µM, respectively (9). Interestingly, $PPII_7$ and $PPII_{11}$ were poor $Mena_{1-112}$ ligands ($K_d$=480 µM and >1 mM, respectively), indicating that the pGolemi α-helix contributes at least 3.5 kcal·mol⁻¹ to the $Mena_{1-112}$ affinity of pGolemi.

Figure 2:
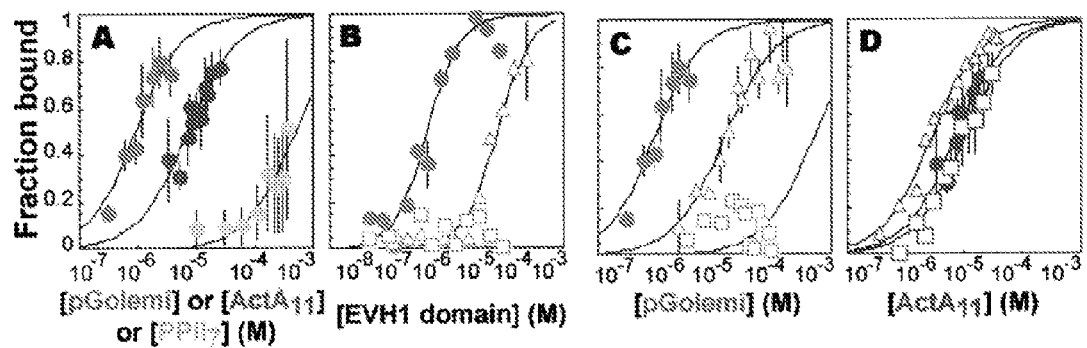

The folded structure of pGolemi also contributes to its ability to differentiate EVH1 domain paralogs (FIG. 2C). The sequences of EHV1 domains $Mena_{1-112}$, $VASP_{1-115}$, and $Evl_{1-115}$ are 60% identical and their structures are virtually superimposable (14). Although $ActA_{11}$ binds equally to all EVH1 domains tested (FIG. 2D, $K_{rel}$<3) pGolemi prefers $Mena_{1-112}$ to $VASP_{1-115}$ ($K_{rel}$=20) and especially to $Evl_{1-115}$ ($K_{rel}$>120) (FIG. 2C). This level of specificity ($K_{rel}$ of 66 and >345, respectively) was confirmed by fluorescence polarization analysis (FIG. 2B). pGolemi also discriminated well between $Mena_{1-112}$ and protein domains that recognize proline-rich sequences or α-helices; its affinity for the KIX domain of CBP, which recognizes α-helical ligands, was 15±0.7 µM; no interaction was detected between pGolemi and the N- or C-terminal SH3 domains of Grb-2 (9).

Figure 3:
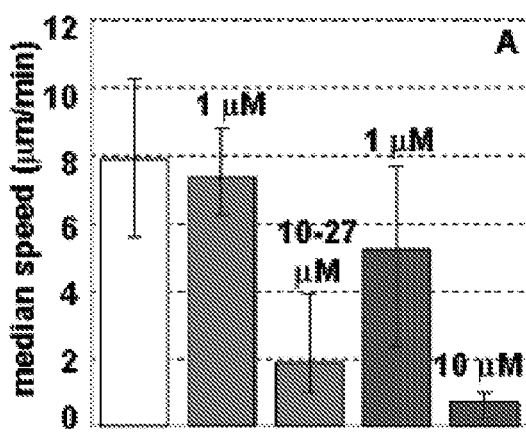

The properties of pGolemi were also examined in *Xenopus laevis* egg cytoplasmic extracts that reconstitute *L. monocytogenes* actin-based motility (FIG. 3) (15). *L. monocytogenes* motility in mammalian cells and extracts is due to interactions between the 639-residue bacterial protein ActA and host proteins that recruit and activate actin polymerization. Addition of 10 µM $ActA_{11}$ decreased the median speed of *L. monocytogenes* by 89%, consistent with previous work. (16, 5b) Addition of 10 or 27 µM pGolemi decreased the median speed of *L. monocytogenes* by 68% (FIG. 3A), but in addition caused extreme speed variations and discontinuous tail formation at all times (FIG. 3C). Discontinuous tails were not observed at any concentration of $ActA_{11}$ tested (FIG. 3D). The differential effects of $ActA_{11}$ and pgolemi on *L. monocytogenes* motility may reflect their different specificities among EVH1 domain family members. Further experimentation will be required to fully understand the molecular events that result in altered motility.

Many protein-protein interactions in cell signaling demand interactions with proline rich sequences (6), and the design of molecules that perturb signaling pathways represents a foremost goal of chemical biology. Our results suggest that miniature proteins based on aPP may represent an excellent framework for the design of ligands that differentiate the roles of EVH1 domains in vitro and in vivo.

REFERENCES (1) (a) Gertler et al., Cell 87:227 (1996); (b) Haffner et al., Embo J. 14 :19 (1995); (c) Reinhard et al., Embo J. 11:2063 (1992)
(2) Gertler et al., Science 248:857 (1990)
(3) Halbrugge et al., Eur. J. Biochem 185:41 (1989)
(4) Callebaut et al., Febs Lett 441:181 (1998)
(5) Reinhard et al., Proc. Natl. Acad. Sci. U.S.A. 92:7956 (1995); (b) Southwick et al., Proc. Natl. Acad. Sci. U.S.A. 91:5168; (c) Niebuhr et al., Embo J. 16:5433 (1997)
(6) Zarrinpar et al., Sci. STKE RE8 (2003)
(7) Williamson, Biochem. J. 297:249 (1994)
(8) (a) Suarez et al., Cell Microbiol. 3:853 (2001; (b) Cameron et al., Nat. Rev. Mol. Cell. Biol. 1:110 (2000);
(9) Please, see supplemental information
(10) (a) Zondlo et al., J. Am. Chem. Soc. 212 :6938 (1999); (b) Chin et al., J. Am. Chem. Soc. 123:2929 (2001); (c) Chin et al., Chem. Int. Ed. Engl. 20:3806 (2001); (d) Chin et al., Bioorg. Med. Chem. Lett. 11:1501 (2001); (e) Montclare et al., J. Am. Chem. Soc. 125:3416 (2003)
(11) Rutledge et al., J. Am. Chem. Soc. in the press (2003)
(12) Koehler et al., J. Am. Chem. Soc. 125:8420 (2003)
(13) Prehoda et al., Cell 97:471 (1999)
(14) Ball et al., Febs Lett. 513:45 (2002)
(15) Theriot et al., Methods Enzymol. 298:114 (1998)
(16) Smith et al., J. Cell Biol. 135:647 (1996)

Incorporation by Reference

All publications and patents mentioned herein are hereby incorporated by reference in their entirety as if each individual publication or patent was specifically and individually indicated to be incorporated by reference.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. An isolated polypeptide selected from the group consisting of:
   (a) an isolated polypeptide comprising amino acid sequence SEQ ID NO: 1; and
   (b) an isolated polypeptide at least 95 percent identical to SEQ ID NO: 1, wherein the polypeptide binds to a protein selected from the group consisting of: *Drosophila* Enabled (Ena), mammalian Mena, vasodilator stimulated phosphoprotein (VASP), Enabled/VASP-like protein (Evl), and Wiskott-Aldrich syndrome protein (WASP).

2. An isolated avian pancreatic polypeptide (aPP) of SEQ ID NO: 1 modified by substitution of at least one and no more than three amino acid residues, wherein at least one of the substituted residues is a substitution of one of positions 1-8 of the aPP of SEQ ID NO: 1, wherein the modified polypeptide binds to a protein selected from the group consisting of: *Drosophila* Enabled (Ena), mammalian Mena, vasodilator stimulated phosphoprotein (VASP), Enabled/VASP-like protein (Evl), and Wiskott-Aldrich syndrome protein (WASP).

3. An isolated avian pancreatic polypeptide (aPP) of SEQ ID NO: 1 modified by substitution of at least one and no more than three amino acid residues, wherein at least one substituted residue is a substitution of position 2 with a hydrophobic residue selected from the group consisting of leucine, isoleucine, valine, or alanine; and wherein the modified polypeptide binds to a protein selected from the group consisting of: *Drosophila* Enabled (Ena), mammalian Mena, vasodilator stimulated phosphoprotein (VASP), Enabled/VASP-like protein (Evl), and Wiskott-Aldrich syndrome protein (WASP).

4. The modified polypeptide of claim 3, wherein at least two and no more than three amino acid residues on the type II polyproline (PPII) helix of the aPP are substituted.

5. The modified polypeptide of claim 3, wherein one of the substitutions is a substitution of at least one amino acid residue in the linker region between the PPII helix and the alpha helix domain of the aPP.

6. The modified polypeptide of claim 5, wherein at least two amino acid residues on the linker region are substituted.

7. The modified polypeptide of claim 3, wherein the modified polypeptide binds to one protein selected from the group consisting of: *Drosophila* Enabled (Ena), mammalian Mena, vasodilator stimulated phosphoprotein (VASP), Enabled/VASP-like protein (Evl), and Wiskott-Aldrich syndrome protein (WASP), but does not bind to the other proteins of this group.

8. The modified polypeptide of claim 3, wherein the at least one amino acid residue substitution is in positions 2, 5, or 8.

9. The modified polypeptide of claim 3, wherein position 1 is proline.

10. The modified polypeptide of claim 3, wherein position 3 is proline.

11. The modified polypeptide of claim 3, wherein position 4 is proline.

12. The modified polypeptide of claim 3, wherein position 6 is proline.

13. The modified polypeptide of claim 3, wherein position 7 is proline.

* * * * *

UNITED STATES PATENT AND TRADEMARK OFFICE
CERTIFICATE OF CORRECTION

PATENT NO. : 7,393,918 B2  Page 1 of 1
APPLICATION NO. : 11/009101
DATED : July 1, 2008
INVENTOR(S) : Dasantila Golemi-Kotra et al.

It is certified that error appears in the above-identified patent and that said Letters Patent is hereby corrected as shown below:

Please insert the following after "Grant GM 59843" in line 15 of Column 1:

-- , Grant GM54160 and Grant GM65453 --

Signed and Sealed this

Twenty-sixth Day of August, 2008

JON W. DUDAS
*Director of the United States Patent and Trademark Office*

SEQUENCE LISTING

<160> NUMBER OF SEQ ID NOS: 10

<210> SEQ ID NO 1
<211> LENGTH: 30
<212> TYPE: PRT

```
<213> ORGANISM: Artificial Sequence
<220> FEATURE:
<223> OTHER INFORMATION: pGolemi, EVH1 domain binding peptide

<400> SEQUENCE: 1

Pro Phe Pro Pro Thr Pro Pro Gly Glu Glu Ala Pro Val Glu Asp Leu
 1               5                  10                  15

Ile Arg Phe Tyr Asn Asp Leu Gln Gln Tyr Leu Asn Val Val
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: F2A, EVH1 domain binding peptide

<400> SEQUENCE: 2

Pro Ala Pro Pro Thr Pro Pro Gly Glu Glu Ala Pro Val Glu Asp Leu
 1               5                  10                  15

Ile Arg Phe Tyr Asn Asp Leu Gln Gln Tyr Leu Asn Val Val
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: T5L, EVH1 domain binding peptide

<400> SEQUENCE: 3

Pro Phe Pro Pro Leu Pro Pro Gly Glu Glu Ala Pro Val Glu Asp Leu
 1               5                  10                  15

Ile Arg Phe Tyr Asn Asp Leu Gln Gln Tyr Leu Asn Val Val
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: F2L, EVHI domain binding peptide

<400> SEQUENCE: 4

Pro Leu Pro Pro Thr Pro Pro Gly Glu Glu Ala Pro Val Glu Asp Leu
 1               5                  10                  15

Ile Arg Phe Tyr Asn Asp Leu Gln Gln Tyr Leu Asn Val Val
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: AllLi, EVH1 domain binding peptide

<400> SEQUENCE: 5

Pro Phe Pro Pro Thr Pro Pro Gly Glu Glu Leu Pro Val Glu Asp Leu
 1               5                  10                  15

Ile Arg Phe Tyr Asn Asp Leu Gln Gln Tyr Leu Asn Val Val
            20                  25                  30

<210> SEQ ID NO 6
<211> LENGTH: 31
```

```
-continued

<212> TYPE: PRT
<213> ORGANISM: Artificial Sequence
<220> FEATURE:
<223> OTHER INFORMATION: segment of avian pancreatic polypeptide

<400> SEQUENCE: 6

Gly Pro Ser Gln Pro Thr Tyr Pro Gly Asp Asp Ala Pro Val Glu Asp
 1               5                  10                  15

Leu Ile Arg Phe Tyr Asn Asp Leu Gln Gln Tyr Leu Asn Val Val
            20                  25                  30

<210> SEQ ID NO 7
<211> LENGTH: 5
<212> TYPE: PRT
<213> ORGANISM: Artificial Sequence
<220> FEATURE:
<221> NAME/KEY: VARIANT
<222> LOCATION: 3, 4
<223> OTHER INFORMATION: Xaa = Any Amino Acid
<220> FEATURE:
<223> OTHER INFORMATION: variant EVH1 binding proline-rich peptide

<400> SEQUENCE: 7

Phe Pro Xaa Xaa Pro
 1               5

<210> SEQ ID NO 8
<211> LENGTH: 11
<212> TYPE: PRT
<213> ORGANISM: Artificial Sequence
<220> FEATURE:
<223> OTHER INFORMATION: ActA11, peptide comprising PPII repeat of ActA
      protein

<400> SEQUENCE: 8

Asp Phe Pro Pro Pro Pro Thr Asp Glu Glu Leu
 1               5                  10

<210> SEQ ID NO 9
<211> LENGTH: 7
<212> TYPE: PRT
<213> ORGANISM: Artificial Sequence
<220> FEATURE:
<223> OTHER INFORMATION: PPII7, segment of SEQ ID NO. 1 that does not
      bind to EVH1

<400> SEQUENCE: 9

Pro Phe Pro Pro Thr Pro Pro
 1               5

<210> SEQ ID NO 10
<211> LENGTH: 11
<212> TYPE: PRT
<213> ORGANISM: Artificial Sequence
<220> FEATURE:
<223> OTHER INFORMATION: PPII11, segment of SEQ ID NO. 1 that does not
      bind to EVH1

<400> SEQUENCE: 10

Pro Phe Pro Pro Thr Pro Pro Gly Glu Glu Ala
 1               5                  10
```